(12) United States Patent
de Lumen et al.

(10) Patent No.: US 6,391,848 B1
(45) Date of Patent: May 21, 2002

(54) SOYBEAN PROTEIN NUTRACEUTICALS

(75) Inventors: Benito O. de Lumen, El Cerrito; Alfredo F. Galvez, Berkeley, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/303,814

(22) Filed: Apr. 30, 1999

(51) Int. Cl.$^7$ .......................... A61K 38/00; A61K 35/78
(52) U.S. Cl. ............................ 514/2; 514/12; 514/783; 530/324; 530/350; 530/378; 530/412; 530/422; 435/69.1
(58) Field of Search .............................. 514/2, 12, 783; 530/324, 350, 378, 412, 422; 435/69.1

(56) References Cited

U.S. PATENT DOCUMENTS 5,614,198 A * 3/1997 Kennedy et al. ......... 424/195.1
6,107,287 A * 8/2000 de Lumen et al. ............. 514/44

OTHER PUBLICATIONS

Odani et al., The Journal Of Biological Chemistry, vol. 262, No. 22, pp. 10502–10505, Aug 5, 1987.*
Yavelow et al., *Proc. Natl. Acad. Sci. USA.,* vol. 82, pp. 5395–5399, Aug. 1985.*
Yavelow et al., *Proc. Natl. Acad. Sci. USA.,* vol. 82, pp. 5395–5399, Aug. 1985.*
Kennedy, *Preventive Medicine,* vol. 22, pp. 796–811, 1993.*
Morita et al., *J. Biochem,* vol. 119, pp. 711–718, 1996.*

* cited by examiner

*Primary Examiner*—Christopher S. F. Low
*Assistant Examiner*—Abdel A. Mohamed
(74) *Attorney, Agent, or Firm*—Richard Aron Osman

(57) ABSTRACT

The invention provides methods and comprisitions for delivering effective amounts of lunasin as a nutraceutical. The general formulation comprises a composition comprising an active unit dosage of a lunasin polypeptide and a pharmaceutically acceptable excipient. The formulations may be delivered or administered by oral ingestion, by topically contacting skin using well known techniques for dermal delivery, by introducing into a retained physiological fluids. The invention also provides methods for making the subject formulations by purifying lunasin polypeptides to the requisite purity, and combining said lunasin polypeptide with a pharmaceuitcally acceptable excipient in an orally active unit dosage. The lunasin source material may be soybeans, a recombinant lunasin polypeptide expression system, a synthetically produced lunasin, or extract or fraction thereof.

14 Claims, No Drawings

SOYBEAN PROTEIN NUTRACEUTICALS

FIELD OF THE INVENTION

The field of the invention is soybean proteins having chemopreventive effects.

BACKGROUND

The concept that dietary factors play an important role in the etiology of different kinds of cancer is well supported by epidemiological data (World Cancer Fund, 1997). For instance, there is much evidence to suggest that diets containing large amount of soybean products are associated with overall low cancer mortality rates, particularly for cancers of the colon, breast and prostate, which has given impetus towards identifying specific compounds in soybean that could be responsible for its cancer preventive effects (Messina and Barnes, 1991; Kennedy, 1995).

A soybean-derived protease inhibitor, Bowman-Birk inhibitor (BBI) has been shown to be a particularly effective chemopreventive agent (Kennedy, 1998). BBI has been characterized as a protein of 8 kD of defined sequence and structure (reviewed by Birk, 1985), however most studies demonstrating the efficacy of BBI have used BBIC, a soybean extract enriched in BBI. BBIC is highly effective in suppressing carcinogenesis (1) induced by several different carcinogens, (2) in three different in animal model systems (rats, mice and hamsters) and in in vitro transformation systems (Kennedy et al, 1993), (3) in several tissues/organs (colon, liver, lung, esophagus and oral epithelium, (4) when administered to animals in several different routes (ip,iv, topical,dietary), (5) involving different kinds of tumors (squamous cell carcinomas, adenocarcinomas, angiosarcomas,etc, (6) in different cell types (epithelial cells in liver, colon, lung, esophagus and cheek pouch as well as connective tissue cells (fibroblasts both in vitro as well as in liver which give rise to angiosarcomas. Thus, the chemopreventive ability of BBIC has been demonstrated in a variety of different carcinogenesis assay systems, achieving Investigational New Drug status from the FDA in 1992 (IND no.34671) and now in human clinical trials.

LITERATURE CITED

Birk (1985) The Bowman-Birk Inhibitor. Int J Peptide Protein Res 25:113–131

Brehm A, Miska E A, McCance D J, Reod J L, Bannister A J and Kouzarides T. (1998) Retinoblastoma protein recruits histone deacetylase to repress transcription. Nature 391:597–601.

Clawson G A (1996) Protease inhibitors and carcinogenesis: A Review. Cancer Investigation 14(6):597–608.

Da Silva Conceicao A, and Krebbers E. (1994). A cotyledon regulatory region is responsible for the spatial expression patterns of Arabidopsis 2S albumin genes. Plant J. 5:493–505.

DePinho R A (1998) The cancer-chromatin connection. Nature 391:533–536.

Erickson, H. P.(1997). FtsZ, a tubulin homologue in prokaryote cell division. Trends in Cell Biol. 7:362–367.

Galvez A F and de Lumen B O (1999) A soybean cDNA encoding a chromatin-binding peptide inhibits mitosis of mammalian cells. Nature Biotechnology 17:495–500.

Galvez A F, Revilleza M J and de Lumen B O (1997) A novel methionine-rich protein from soybean cotyledon: cloning and characterization of cDNA (Accession No. AF005030) Plant Gene Register. Plant Physiol 114:1567.

Harlow E and Lane D (1988) Antibodies: A lab manual. p. 342. Cold Spring Harbor Lab.

Hassig C A, Fleischer T C, Billin A N, Schreiber S L and Ayer D E (1997) Histone deacetylase is required for full transcriptional repression by mSin3A. Cell 89:341–347.

Hauxwell A J, Corke F M K, Hedley C L and Wang J. (1990). Storage protein gene expression is localized to regions lacking mitotic activity in developing pea embryos: An analysis of seed development in *Pisum sativum* XIV. Development 110:283–289.

Kennedy A R (1993a) Cancer prevention by protease inhibitors. Preventive Med 22:796–811.Kennedy A R (1993b) Potential mechanisms of antitumorigenesis by protease inhibitors. in. Antimutagenesis and Anticarcinogenesis Mechanisms III, pp. 301–307. G. Bronzetti et al (eds). Plenum Press, New York.

Kennedy A R (1994) Prevention of carcinogenesis by protease inhibitors. Cancer Res (Suppl) 54:1999S–2005S.

Kennedy A R (1995) The evidence for soybean products as cancer preventive agents. J Nutr 125:733S–743S.

Kennedy A R (1998) The Bowman-Birk inhibitor from soybeans as an anticarcinogenic agent. Am J Clin Nutr 68 (suppl):1406–1412S.

Kennedy A R and Little J B (1978) Protease inhibitors suppress radiation induced malignant transformation in vitro. Nature (Lond) 276:825–826.

Kennedy A R, B F Szuhaj, P Newberne and Billings P C (1993) Preparation and production of a cancer chemopreventive agent, Bowman-Birk inhibitor concentrate. Nutr Cancer 19:281–302.

Laherty C D, Yang W M, Sun J M, Davie J R, Seto E and Eisenman R N (1997) Histone deacetylases associated with the mSin3 corepressor mediate mad transcriptional repression. Cell 89:349–356.

Magnaghi-Jaulin L, Groisman R, Naguibneva I, Robin P, Lorain S, Le Villain J P, Troalen F, Trouche D and Harel-Bellan A.(1998) Retinoblastoma protein represses transcription by recruiting a histone deacetylase. Nature 391:601–605.

Messina M and Barnes S (1991) The role of soy products in reducing risk of cancer. J Natl Cancer Institute 83:541–546.

Odani, S., Koide, T and Ono, T. 1987. Amino acid sequence of a soybean (Glycine max) seed polypeptide having a poly(L-aspartic acid) structure. J. Biol. Chem. 262, 10502–10505.

Pazin M and Kadonaga J T (1997) What's up and down with histone deacetylation and transcription? Cell 325–328.

Spencer D and Higgins T J V. (1981). Molecular aspects of seed protein biosynthesis. In Commentaries in Plant Science, ed. Smith H. (pergamon Press, New York) Vol. 2 pp. 175-189. World Cancer Fund/American Institute for Cancer Research (1997) Food, nutrition and the prevention of cancer: A global perspective. American Institute of Cancer Research. Washington D.C.

Yavelow J, Collins M, Birk Y, Troll W and Kennedy A R (1985) Nanomolar concentrations of Bowman-Birk protease inhibitor suppress X-ray induced transformation in vitro. Proc Natl Acad Sci USA 82:5395–5399.

Yavelow J, Finlay T H, Kennedy A R and Troll W. (1983) Bowman-Birk soybean protease inhibitor as an anticarcinogen. Cancer Research (SUPPL) 43:24545–2459.

SUMMARY OF THE INVENTION

The invention provides methods and comprisitions for delivering effective amounts of lunasin as a nutraceutical. The general formulation comprises a composition comprising an active unit dosage of a lunasin polypeptide and a pharmaceutically acceptable excipient, said composition comprising at least 50% by polypeptide weight said lunasin polypeptide and less than 10% by polypeptide weight Bowman-Birk Inhibitor polypeptide. In other embodiments, the composition comprises at least 70%, preferably at least 90%, more preferably at least 98%, most preferably 100% by polypeptide weight said lunasin polypeptide and less than 2%, preferably less than 0.5%, more preferably less than 0.1%, most preferably 0% by polypeptide weight Bowman-Birk Inhibitor polypeptide. The formulations may be delivered or administered by any of a wide variety of convenient delivery methods well known in the art, (see, e.g. Goodman and Gilman's The Pharmacological Basis of Therapeutics, Ninth Edition) including oral ingestion, by topically contacting skin using well known techniques for dermal delivery, by introducing into a retained physiological fluids such as blood, synovial fluid, interstitial fluid, etc.

The invention also provides methods for making the subject formulations by purifying lunasin polypeptides to the requisite purity, and combining said lunasin polypeptide with a pharmaceuitcally acceptable excipient in an orally active unit dosage. The lunasin source material may be soybeans, a recombinant lunasin polypeptide expression system, a synthetically produced lunasin, or extract or fraction thereof. Suitable excipients and dosages are readily determined emperically as guided by existing BBIC data.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

We have shown that a small subunit peptide of a 2S albumin isolated from soybean seed, which we named lunasin, has an antimitotic effect when expressed in mammalian cells (Galvez A F and de Lumen B O, 1999 and U.S. Ser. No. 08/938,675). Unlike other antimitotic agents that disrupt microtubule function, we have shown that when the lunasin gene is transfected and expressed inside the cell, lunasin preferentially binds to hypoacetylated chromatin in lunasin-transfected cells, leading to the displacement of kinetochore proteins during mitosis.

The lunasin polypeptide also contains a functional RGD (arg-gly-asp) motif. When exogenously applied to mammalian cell cultures, lunasin through the RGD tripeptide binds to cell membrane integrins and subsequently gets into the cytoplasm through membrane turnover. The relatively small amounts of lunasin that gets into the nucleus by passive diffusion and at prometaphase (when nuclear membrane breakdown occurs) are sufficient to effectively bind regions of hypoacetylated chromatin. However, unlike lunasin-transfected cells that constitutively express lunasin in high amounts, internalized lunasin appears not to affect kinetochore assembly as the cells undergo normal mitosis. Instead, lunasin inhibits the transformation of normal embryo fibroblast cells into cancerous tumors by carcinogenic agents. The binding affinity of lunasin to regions of deacetylated nucleosomes is consistent with an anticarcinogenic role of lunasin as a surrogate tumor suppressor by preventing chromatin acetylation and oncogene activation in cells with mutated tumor suppressor genes. The cell adhesion property of lunasin also confers an added benefit of preventing the spread of cancer by competitively binding to membrane integrins required by metastatic cells for attachment to the extracellular matrix and for proliferation.

We also demonstrated that the protease inhibitor Bowman-Birk Inhibitor (BBIC) derived from soybean, which has been shown to be chemopreventive against different types of cancers in in vitro and in vivo animal models, contains lunasin as a major component. In fact, the removal of lunasin from BBIC by immuno-depletion significantly reduced the ability of BBIC to inhibit carcinogen-mediated transformation of C3H cells. In addition, using equimolar amounts, lunasin was found to be more effective than BBIC in preventing carcinogen-induced tumor formation. These findings indicate that lunasin is an, if not the, active anticarcinogenic constituent of BBIC.

Accordingly, as used herein the term lunasin refers to compounds comprising the natural soybean lunasin polypeptide (coincidentally purified and sequenced by Odani et al., 1987 (Ser Lys Trp Gln His Gln Gln Asp Ser Cys Arg Lys Gln Leu Gln Gly Val Asn Leu Thr Pro Cys Glu Lys His Ile Met Glu Lys Ile Gln Gly Arg Gly Asp Asp Asp Asp Asp Asp Asp Asp Asp, SEQ ID NO:1) and active fragments thereof comprising at least the Arg-Gly-Asp motif followed by at least an hexa-Asp/Glu motif. Preferred lunasin polypeptides comprise residues 33–43, preferably 21–43, more preferably 10–43 and most preferably 1–43 of SEQ ID NO:1. Exemplary lunasin-del compounds include (again using N→C nomenclature convention) shown to be effective at inhibiting carcinogenesis in in vitro and animal models include:

lunasin-del-1: MRG—residues 32–43 of SEQ ID NO:1 fusion lunasin-del-2: α-tubulin—residues 32–43 of SEQ ID NO:1 fusion lunasin-del-3: β-tubulin—residues 27–42 of SEQ ID NO:1 fusion lunasin-del-4: MAP2—residues 5–43 of SEQ ID NO:2 fusion lunasin-del-5: Mapmodulin—residues 32–43 of SEQ ID NO:1 fusion lunasin-del-6: GFP—residues 32–43 of SEQ ID NO:1 fusion lunasin-del-7: MAP4—residues 23–42 of SEQ ID NO:1 fusion lunasin-del-8: FLAGG—residues 9–43 of SEQ ID NO:1 fusion lunasin-del-9: CYCLIN A—residues 32–43 of SEQ ID NO:1 fusion lunasin-del-10: CYCLIN B1—residues 32–43 of SEQ ID NO:1 fusion lunasin-del-11: CYCLIN B2—residues 19–42 of SEQ ID NO:1 fusion lunasin-del-12: CYCLIN B3—residues 13–43 of SEQ ID NO:1 fusion lunasin-del-13: SH2—octa-aspartate fusion lunasin-del-14: SH3—octa-aspartate fusion lunasin-del-15: SEQ ID NO:1, residues 27–34—MRG-octa-aspartate fusion lunasin-del-16: SEQ ID NO:1, residues 27–34—SEQ ID NO:1, residues 27–34—octa-aspartate fusion lunasin-del-17: MRG-tetrta-aspartate-tetra glutamate fusion Lunasin Peptide Inhibits Carcinogen-mediated Transformation of C3H 10T1/2 Mouse Fibroblast Cells Into Tumor Cells. Experiments done using the same in vitro transformation assay used to determine the chemopreventive property of BBIC showed that the exogenous application of the lunasin peptide to as low as 10 nM (10 nM to 10 mM)

inhibits the transformation of normal mouse embryo fibroblast cells (C3H 10T1/2) into tumorous foci by carcinogenic agents, MCA (3-methylcholanthrene) and DMBA (7,12-dimethylbenz[a]anthracene). Deletion of the acidic carboxyl end (lunasin-del-C) and the RGD cell adhesion motif (lunasin-GRG) removes the inhibition effect indicating that these domains are essential.

Lunasin is a Major Component of the Bowman-Birk Protease Inhibitor (BBIC) from Soybean, a Known Cancer Preventive Substance. Protease inhibitors, unlike other potential classes of cancer preventive that have been studied, have several features that we found to be also true for lunasin. The most dramatic difference is their ability to affect carcinogenesis in an irreversible way. When the administration of BBIC is stopped in either in vitro or in vivo experiments, malignant cells or tumors do not arise in the assay systems used (Kennedy, 1994). In contrasts, chemopreventive agents such as vitamin E, b-carotene and retinoids have a reversible effect on in vitro systems—transformed cells do arise when these chemopreventive agents are removed from carcinogen-treated cultured cells. Protease inhibitors are also unlike other chemopreventive agents in that they are effective at extremely low levels (nM) while the other agents are effective only at very high levels (mM). The dose response of BBIC suppression of carcinogenesis is unusual in that dose levels of BBIC have the same suppressive effects over a range varying over several orders of magnitude. Thirdly, the striking ability of protease inhibitors to suppress so many different cancers make them different from most chemopreventive agents. Their anticancer properties are not restricted to specific organs/tissues.

Lunasin, like BBIC, belongs to the same class of 2S albumins family and both are prepared in similar ways. We found by Western blot analysis that lunasin is a major component of commercially available BBIC preparations (Sigma). In an exemplary blot, lane 3 which contained a crude preparation of trypsin inhibitor (Sigma T 9128, Type II-S Soybean soluble powder) showed a major protein band at 16 kDa that lighted up in the immunoblot. BBI is an 8 kDa protein that is known to dimerize in solution. Lane 4 containing BBIC (Sigma T9777, Bowman-Birk Inhibitor, from soybean lyophilized powder) showed two protein bands, 8 kDa and 16 kDa, which both lighted up in immunoblot. Lunasin which has 2 cysteine residues can form disulfide linkages with BBI (as a monomer and a dimer) which has 14 cysteine residues. This clearly shows that lunasin is found in BBIC as a major component. Furthermore, we showed that removal of lunasin from BBIC by lunasin antibody affinity column and by resin treatment significantly reduced the ability of BBIC to inhibit transformation of C3H cells. This evidence together with the ability of lunasin to inhibit carcinogen-mediated transformation of C3H cells indicates that lunasin is a major if not the major active chemopreventive molecule in BBIC. In fact, our data indicate that BBIC may act to protect lunasin from being digested in the gastrointestinal tract. The ability of lunasin to get inside mammalian cells then modulate chromatin function now provides a rational mechanism to explain the chemopreventive property of BBIC as well as guidance for the use in lunasin as a neutraceutical or nutritional supplement, in particular as an anticarcinogenic agent. For example, substituting lunasin for BBI at comparable dosages and routes of administration provides efficacy in cell and animal studies (see, U.S. Pat. Nos. 5,618,679; 5,616,492; 5,614,198; 5,505,946; 5,376,373; 5,338,547).

Chromatin Modification and Tumor Suppression. Our hypothesis is that the chromatin-binding ability of lunasin is the underlying mechanism behind the antimitotic property of the lunasin gene and the cancer preventive property of lunasin peptide. A series of studies strongly suggest that chromatin modification is linked with tumor suppression pathways. (DePinho,1998; Brehm et al, 1998; Magnaghi-Jaulin, 1998; Pazin and Kadonaga, 1997; Hassig et al, 1997; Laherty et al, 1997). For instance, the retinoblastoma protein Rb is complexed with E2F (a family of transcription factors controlled by Rb) and HDAC1 (the major mammalian histone deacetylase which modulates chromatin structure) in mammalian cells. Rb represses E2F-regulated promoter by recruiting HDAC1 which deacetylates core histones causing a tighter association between DNA and nucleosomes, thus impairing the binding of transcription factors to recognition elements in DNA. The Rb/HDAC/E2F complex could be the target for transforming viruses leading to the release of suppression and a fully transformed state. The binding of lunasin to the hypoacetylated region of chromatin may suppress tumorigenesis in a different context. While deacetylation causes tighter association of DNA with nucleosomes in condensed chromosomes leading to a change in higher order structure, it also exposes positive charges on lysine residues that would allow lunasin to bind to histone terminal sequences and prevent the reversible acetylation/deacetylation process. Consequently, gene expression is more or less permanently repressed. Animal studies show that lunasin effectively survives digestion, gets absorbed and ends up in the tissues. Our evidence shows that lunasin gets internalized in the cell via the RGD motif (i.e. there is no internalization when the -RGD-motif is deleted) and gets inside the nucleus through passive diffusion because of its 4 kDa size and at prometaphase when the nuclear envelope breaks down. Eventually, lunasin binds to the core histones of the nucleosomes and inhibit transformation of the cell in the presence of carcinogens by repressing transcription as described above.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A formulation comprising a composition comprising an active unit dosage of a lunasin polypeptide and a pharmaceutically acceptable excipient, said composition comprising at least 50% by polypeptide weight said lunasin polypeptide and less than 10% by polypeptide weight Bowman-Birk Inhibitor polypeptide.

2. A formulation according to claim 1, wherein the composition comprises at least 90% by polypeptide weight said lunasin polypeptide and less than 1% by polypeptide weight Bowman-Birk Inhibitor polypeptide.

3. A formulation according to claim 1, wherein the lunasin polypeptide comprises residues 33–43 of SEQ ID NO:1.

4. A formulation according to claim 1, wherein the lunasin polypeptide comprises residues 21–43 of SEQ ID NO:1.

5. A formulation according to claim 1, wherein the lunasin polypeptide comprises residues 10–43 of SEQ ID NO:1.

6. A formulation according to claim 1, wherein the lunasin polypeptide comprises residues 1–43 of SEQ ID NO:1.

7. A formulation according to claim 1, wherein the lunasin polypeptide consists of residues 1–43 of SEQ ID NO: 1.

8. A method for administering a lunasin polypeptide, comprising the step of orally administering a formulation according to claim 1, 2, 3, 6, or 7.

9. A method for administering a lunasin polypeptide, comprising the step of topically contacting skin with a formulation according to claim 1, 2, 3, 6, or 7.

10. A method for administering a lunasin polypeptide, comprising the step of introducing into a retained physiological fluid a formulation according to claim 1, 2, 3, 6 or 7.

11. A method for making a formulation according to claim 1 comprising the steps of:

purifying a lunasin polypeptide to at least 50% polypeptide weight said lunasin polypeptide and less than 10% by polypeptide weight Bowman-Birk Inhibitor polypeptide, and combining said lunasin polypeptide with a pharmaceutically acceptable excipient in an orally active unit dosage.

12. A method according to claim 11, wherein the lunasin polypeptide is purified from soybeans or extract or fraction thereof.

13. A method according to claim 11, wherein the lunasin polypeptide is purified from a recombinant lunasin polypeptide expression system or extract or fraction thereof.

14. A method according to claim 11, wherein the lunasin polypeptide is purified from a synthetically produced lunasin, or extract or fraction thereof.

* * * * *

UNITED STATES PATENT AND TRADEMARK OFFICE
CERTIFICATE OF CORRECTION

PATENT NO. : 6,391,848 B1
DATED : May 21, 2002
INVENTOR(S) : de Lumen et al.

It is certified that error appears in the above-identified patent and that said Letters Patent is hereby corrected as shown below:

Column 6,
Lines 50-51, delete "comprising an active unit dosage of a lunasin" and insert -- which delivers an effective amount of a lunasin polypeptide as a nutraceutical comprising an active dosage of said lunasin --

Signed and Sealed this

Twenty-fourth Day of September, 2002

*Attest:*

JAMES E. ROGAN
*Attesting Officer*           *Director of the United States Patent and Trademark Office*